(12) United States Patent
Plank

(10) Patent No.: US 7,410,055 B2
(45) Date of Patent: Aug. 12, 2008

(54) TRANSPORT CONTAINER FOR SLIDES FOR IMMUNOLOGICAL LABELING FOR THIN TISSUE SECTIONS

(75) Inventor: Heinz Plank, Wr. Neudorf (AT)

(73) Assignee: Leica Mikrosysteme GmbH, Vienna (AT)

( * ) Notice: Subject to any disclaimer, the term of this patent is extended or adjusted under 35 U.S.C. 154(b) by 380 days.

(21) Appl. No.: 10/784,461

(22) Filed: Feb. 23, 2004

(65) Prior Publication Data

US 2004/0171141 A1 Sep. 2, 2004

(30) Foreign Application Priority Data

Feb. 28, 2003 (DE) ................. 103 09 210

(51) Int. Cl.
  *B65D 85/48* (2006.01)
(52) U.S. Cl. .................. 206/456; 206/509; 206/565
(58) Field of Classification Search ................ 206/363, 206/438, 449, 564, 453–456, 713–716, 722–724, 206/503, 509, 511, 565
  See application file for complete search history.

(56) References Cited

U.S. PATENT DOCUMENTS

| | | | |
|---|---|---|---|
| 2,501,379 A | 3/1950 | Cranston | |
| 3,469,686 A * | 9/1969 | Gutsche et al. | 206/564 |
| 3,478,867 A | 11/1969 | Weiss | |
| 3,746,161 A | 7/1973 | Jones | |
| 3,756,393 A | 9/1973 | Markwitz et al. | |
| 3,773,183 A | 11/1973 | Johnson | |
| 3,802,555 A | 4/1974 | Grasty et al. | |
| 4,077,515 A | 3/1978 | Shoberg | |
| 4,085,845 A | 4/1978 | Perfect | |
| 4,127,189 A * | 11/1978 | Shumrak et al. | 206/520 |
| 4,159,875 A | 7/1979 | Hauser | |
| 4,207,980 A | 6/1980 | Namiki | |
| 4,440,301 A | 4/1984 | Intengan | |
| 4,589,551 A | 5/1986 | Hellen | |
| 4,682,891 A | 7/1987 | De Macario et al. | |
| 4,836,667 A | 6/1989 | Ozeki | |
| 4,883,195 A * | 11/1989 | Ott et al. | 206/815 |
| 4,919,894 A | 4/1990 | Daniel | |
| 5,079,172 A | 1/1992 | Hari et al. | 436/518 |
| 5,090,568 A | 2/1992 | Tse | |
| 5,143,714 A | 9/1992 | Cosgrove et al. | 424/3 |
| 5,310,076 A * | 5/1994 | Burton et al. | 206/723 |
| 6,076,681 A * | 6/2000 | Chenoweth | 206/714 |
| 6,118,582 A | 9/2000 | Del Buono | |
| 6,179,127 B1 * | 1/2001 | Kato et al. | 206/714 |
| 6,199,715 B1 * | 3/2001 | Hayes et al. | 206/564 |

(Continued)

FOREIGN PATENT DOCUMENTS

DE 38 78 167 T2 5/1993

(Continued)

*Primary Examiner*—Luan K Bui
(74) *Attorney, Agent, or Firm*—Simpson & Simpson, PLLC

(57) ABSTRACT

A transport container (40) for slides (4) for immunological labeling of thin tissue sections (2a) is disclosed. The transport container (40) is embodied in the form of a trough which comprises a peripheral delimiting wall (49) that is closed off by a base (50). There is embodied in the interior of the trough on the delimiting wall (49) at least one peripheral step (57) on which the slide rests and is spaced away from the base (50) of the transport container (40).

9 Claims, 6 Drawing Sheets

U.S. PATENT DOCUMENTS

| | | | |
|---|---|---|---|
| 6,293,404 B1 * | 9/2001 | Bloom | 206/714 |
| 6,296,122 B1 * | 10/2001 | Nakazono et al. | 206/707 |
| 6,446,807 B1 * | 9/2002 | Lafond et al. | 206/456 |
| 6,863,179 B2 * | 3/2005 | Leykin et al. | 206/565 |
| 6,946,287 B2 | 9/2005 | Streit et al. | |
| 2002/0029989 A1 * | 3/2002 | Anthony et al. | 206/366 |

FOREIGN PATENT DOCUMENTS

| | | |
|---|---|---|
| DE | 299 06 382 U1 | 9/1999 |
| DE | 19923584 | 12/2000 |
| EP | 0415400 | 3/1991 |
| EP | 0 317 001 B1 | 2/1993 |
| GB | 2009045 | 6/1979 |
| WO | WO02/058850 | 8/2002 |

\* cited by examiner

TRANSPORT CONTAINER FOR SLIDES FOR IMMUNOLOGICAL LABELING FOR THIN TISSUE SECTIONS

CROSS REFERENCE TO RELATED APPLICATIONS

This application claims priority of the German patent application 103 09 210.2 which is incorporated by reference herein.

FIELD OF THE INVENTION

The present invention concerns a transport container for slides for immunological labeling for thin tissue sections.

BACKGROUND OF THE INVENTION

To allow examination of the structure of biological samples such as tissues or cells using an electron microscope or high-resolution optical microscope methods, ultrathin sections (only a few nm thick) are prepared and are applied onto specimen carrier grids (hereinafter referred to as metal grids) made of metal, preferably of nickel. For microscopic examination the sections are contrasted, or individual constituents of the sample are labeled using special cytochemical methods. These cytochemical methods are often based on the principle of ligand pair formation: a first ligand can be contained in the biological sample, and the second ligand, when it comes into contact with that sample, then binds as a binding partner to the first ligand. Examples of biologically based ligand pairs include antigen/antibody binding pairs, enzyme/substrate binding pairs, lectins/sugars, hormone/receptor systems, and DNA/DNA and DNA/RNA pairs.

Numerous methods involving the antigen/antibody binding pair are known in the existing art; these are grouped under the heading of immunohistochemistry and immunocytochemistry (hereinafter referred to as immunological labeling techniques). U.S. Pat. No. 5,143,714, for example, discloses a method that adsorbs an antigen out of a liquid sample in a pelletizable gel substance. The gel pellet is surrounded by a diffusion barrier, integrated as a block into a stamped-out gel matrix, and subsequently subjected to immunological labeling techniques just like a tissue sample. DE 38 78 167 T2 describes the use of colloidal gold particles to label ligands, using the immunogold staining technique. A greatly improved method that permits qualitative and quantitative evaluation of an antigen in a sample is disclosed in U.S. Pat. No. 5,079,172 in the form of a sandwich assay, in which the first antibody that binds the antigen is labeled with a gold-labeled second antibody that binds the first antibody. Using electron-microscopy evaluation methods, the antigen attached in the sample can be determined qualitatively and quantitatively based on the quantity of gold particles.

A characteristic shared by many immunohistochemical and immunocytochemical protocols for immunological labeling of thin tissue sections is the fact that they usually comprise ten to 20 individual process steps. Most of the process steps comprise operations in which the sample under examination is washed with a buffer solution or labeling solution.

At present, these washing operations are performed manually, in a laborious process in which individual droplets of the aqueous buffer solution or labeling solution are applied with a pipette onto a hydrophobic substrate (e.g. Parafilm®, Parlodion®, Colloidion, or Formfan®). The metal grids with the thin tissue sections are individually laid down thereonto in order to react with the treatment liquid. Because of the light weight of the metal grid and the surface tension of the liquid droplet, the metal grid floats on the droplet surface. After a certain residence time for this step (often 5 to 10 min), the metal grid is transported with tweezers to the next droplet. This operation is continued up to the last position of the standard protocol, and occupies a technician for as long as several hours for each immunological labeling reaction.

It is readily apparent that this manual process requires constant attention by the operator, and entails high labor costs because of the large time requirement. The number of samples to be processed simultaneously is greatly limited, and errors by the operator while precisely pipetting and positioning liquid droplets with very small volumes cannot be excluded. The manual method cannot rule out confusion of samples after the long processing time during immunological labeling; this could be prevented by using a sample carrier having an identifier in the form of a chip or barcode, as presented in German Utility Model DE 299 06 382 U1.

In addition, evaporation of the liquid droplets during longer-duration standard protocols constitutes a major problem.

Although German Utility Model DE 298 17 912 U1 discloses an apparatus for washing microscopable preparations on supports after immunocytochemical treatment, it refers to a wash box in which a larger quantity of washing solution flows through at a certain flow rate over the preparation and carrier. This apparatus is not suitable for the implementation of immunological labeling techniques themselves, since the antibody-containing labeling solutions that are used are very expensive and are therefore employed in only the smallest possible volumes.

A transport container for slides that is suitable for and can be used for automatic implementation of immunological labeling techniques for thin tissue sections is not presently known.

SUMMARY OF THE INVENTION

It is therefore the object of the invention to make available a transport container for slides for immune labeling of thin tissue sections that is suitable for an automatic treatment process and ensures reliable, error-free handling of the thin tissue sections on the slide.

The object is achieved, by a transport container for slides for immunological labeling of thin tissue sections, comprising: a peripheral delimiting wall, a base is attached to the peripheral delimiting wall, wherein the base closes off the transport container, and at least one peripheral step formed in the interior of the transport container, wherein the slide rests and is spaced away from the base of the transport container.

The object is achieved as well by a transport container for slides for immunological labeling of thin tissue sections, comprising: a peripheral delimiting wall which is constituted by a left and a right sidewall that are both joined to one another via a back wall and a front wall, a base is attached to the peripheral delimiting wall, wherein the base closes off the transport container, at least one peripheral step formed in the interior of the transport container, wherein the slide rests and is spaced away from the base of the transport container, and a grip recess is formed in the left and the right sidewall close to the front wall.

The transport container according to the present invention is particularly advantageous because the transport container is embodied in the form of a trough, the trough comprising a peripheral delimiting wall that is closed off by a base. When the transport containers are arranged in a stack, it is particularly advantageous that the base of one transport container constitutes the cover of a transport container arranged beneath it. Stacking of the transport containers is particularly advantageous because evaporation of the liquid droplets applied on the slide is thereby prevented. To ensure a certain moisture level in the enclosed space around the slides, a moisture-emitting medium is placed in the transport container. The transport container is embodied in the form of a trough which comprises a peripheral delimiting wall that is closed off by a base. Embodied in the interior of the trough on the delimiting wall is at least one peripheral step on which the slide rests and is spaced away from the base of the transport container. The peripheral delimiting wall of the transport container is constituted by a left and a right parallel sidewall that are both joined to one another via a back wall and a front wall. Embodied on the base of the transport container are a first and a second elevation, each of which possesses a planar flattened area that is located at the level of the step on which the slide rests, resulting in additional support of the slide.

It is advantageous that the transport container for slides for immunological labeling of thin tissue sections, comprising: a peripheral delimiting wall which is constituted by a left and a right sidewall that are both joined to one another via a back wall and a front wall, a base is attached to the peripheral delimiting wall, wherein the base closes off the transport container, at least one peripheral step formed in the interior of the transport container, wherein the slide rests and is spaced away from the base of the transport container, and at least one protrusion is formed in the left or the right sidewall, wherein the protrusion is configured such that the slide does not contact the left or right sidewall in the region of the protrusion.

BRIEF DESCRIPTION OF THE DRAWINGS

The invention will be elucidated below with reference to the examples depicted schematically in the FIGS., in which:

FIG. 8 is a sectioned view of the transport container taken along dashed line 8-8 in FIG. 7a.

DETAILED DESCRIPTION OF THE INVENTION

Figure 1:
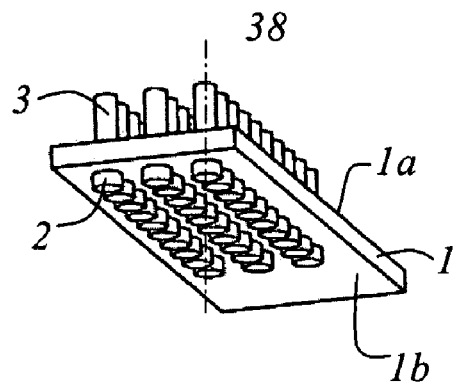
FIG. 1 is a perspective view of a carrier plate that carries a plurality of metal grids.

FIG. 1 shows a carrier plate 1 that defines an upper side 1a and a lower side 1b. On lower side 1b, carrier plate 1 possesses marked positions at which metal grids 2 having thin tissue sections 2a (see FIG. 3) are positioned. The positions of metal grids 2 on carrier plate 1 are elevated. This prevents liquid bridges from forming between the individual metal grids 2 upon contact with the liquid droplets. Located on upper side 1a of carrier plate 1, opposite the positions of metal grids 2, are orifices 3a (see FIG. 3) which contain magnets 3, for example permanent magnets. They cause metal grids 2 to be held in place on lower side 1b of carrier plate 1 by magnetic force. The spacing between metal grid 2 and magnet 3 should be kept as small as possible (<2 mm). Carrier plate 1 is preferably made of a dimensionally stable nonmagnetic material, preferably aluminum, brass, or fiber-reinforced plastics, and advantageously is hydrophobically coated (e.g. with a Teflon pressure coating) on lower side 1b that carries metal grids 2. It is self-evident to one skilled in the art that numerous embodiments are possible in terms of the shape of carrier plate 1 and the arrangement of metal grids 2 on carrier plate 1. In the embodiment depicted here, a rectangular plate having dimensions of approx. 76×26 mm (3×1 inch; microscope slide size) accommodates, for example, 10×3 metal grids 2 having a diameter of 3 mm. It is critical that the positions of metal grids 2 on lower side 1b of carrier plate 1 be located opposite the orifices for magnets 3 on upper side 1a of carrier plate 1, and preferably also be located opposite the positions of at least one liquid droplet 6 on upper side 4a of a slide 4 (see FIG. 2).

In a further exemplary embodiment, metal grids 2 are held on lower side 1b of carrier plate 1 by electromagnets (not depicted).

Figure 2:
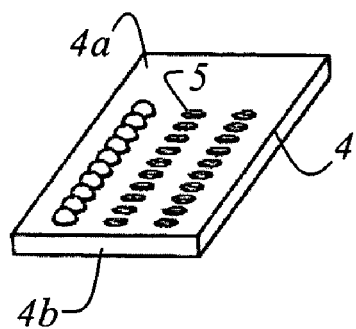
FIG. 2 is a perspective view of a slide having depressions that can be filled with at least one treatment liquid.

FIG. 2 is a perspective view of slide 4 according to the present invention, which defines an upper side 4a and a lower side 4b. Slide 4 possesses on upper side 4a multiple depressions 5 (called "wells") that, in the embodiment shown, are arranged in rows and are each filled with a liquid droplet 6. Liquid droplet 6 comprises a washing solution or treatment solution as disclosed in the existing art. Provision is also made for different liquids to be present in the individual depressions 5 (e.g. one row of depressions 5 filled with washing solution, the next row of depressions 5 filled with labeling solutions having various antibodies). Slide 4 is advantageously transparent and is made of dimensionally stable material. Slide 4 is preferably made of glass or plastic, and is hydrophobically coated (e.g. with a Teflon pressure coating 5a) on upper side 4a that carries depressions 5 and in depressions 5 themselves. Depression 5 is identical in depth to thickness D (see FIG. 3) of Teflon coating 5a. Depression 5 is advantageously approx. 50 µm in size. Depressions 5 carry liquid droplets 6 having a volume that varies between 50 µl and 5 µl. The volume of liquid droplets 6 for washing solution is greater than the volume of the liquid droplets that contain antibodies and/or gold. The reason for the reduced volume with antibodies or gold solution is that the cost of such solutions is high. The Teflon pressure coating is the same for the various droplet sizes. Liquid droplets 6 bulge upward to a greater or lesser extent because of the hydrophobic rim coating. In order to bring the grids into contact with these droplets, it is absolutely necessary in terms of the procedure to know the droplet size, since the droplet size results in a different position for the lowering motion of metal grids 2.

Figure 3:
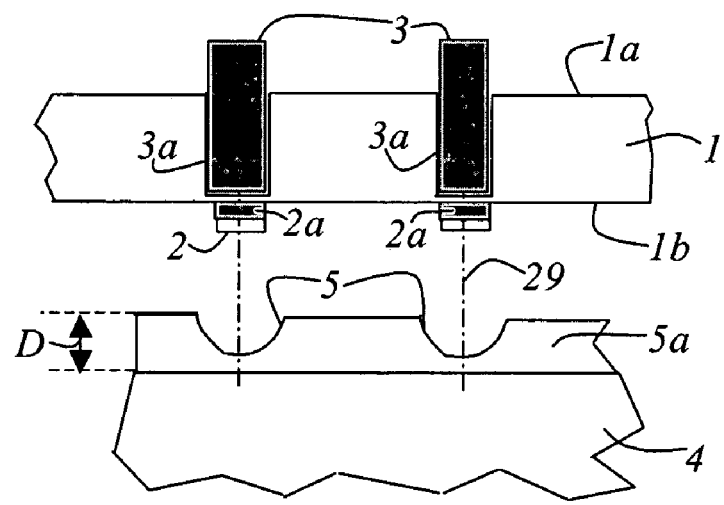
FIG. 3 is a schematic sectional view that illustrates the spatial correlation of the carrier plate with the slide.

The spatial correlation between slide 4 and carrier plate 1 is depicted in FIG. 3 in a partial cross-sectional view. The partial cross-sectional view is defined, for example, in FIG. 1 by dashed line 38. In the exemplary embodiment shown here, a hydrophobic coating 5a having a thickness D is applied on slide 4. Orifices 3a for magnets 3 are provided in carrier plate 1. Samples or thin tissue sections 2a are provided at marked positions on lower side 1b of carrier plate 1. Adjoining each thin tissue section 2a is a metal grid 2. Metal grid 2, and thus also thin tissue section 2a, are held in position by the associated magnets 3. Dot-dash line 29 in FIGS. 1 and 3 illustrates the fact that carrier plate 1 and slide 4 are arranged in such a way that each thin tissue section 2a with metal grid 2 lies opposite a depression 5 on slide 4.

Figure 4A:
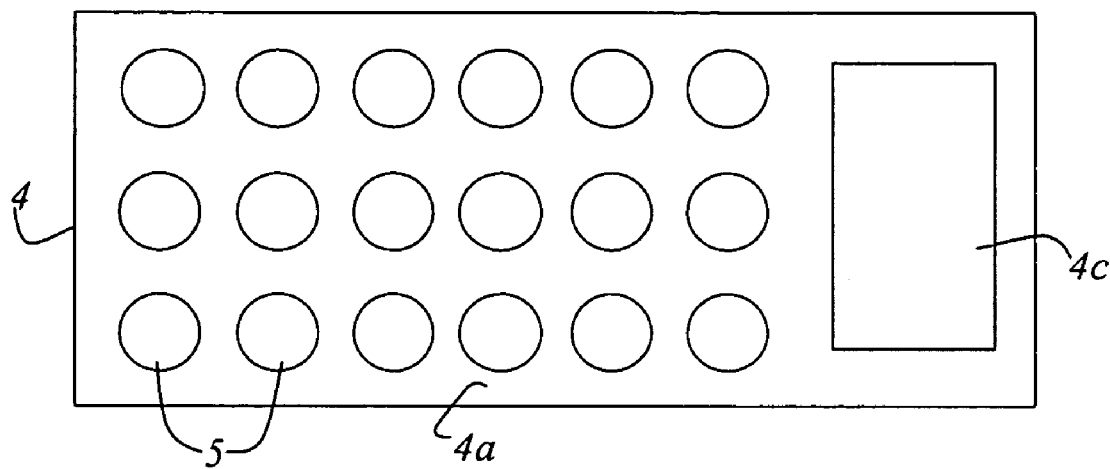
FIG. 4a is a plan view of an embodiment of a slide.
Figure 4B:
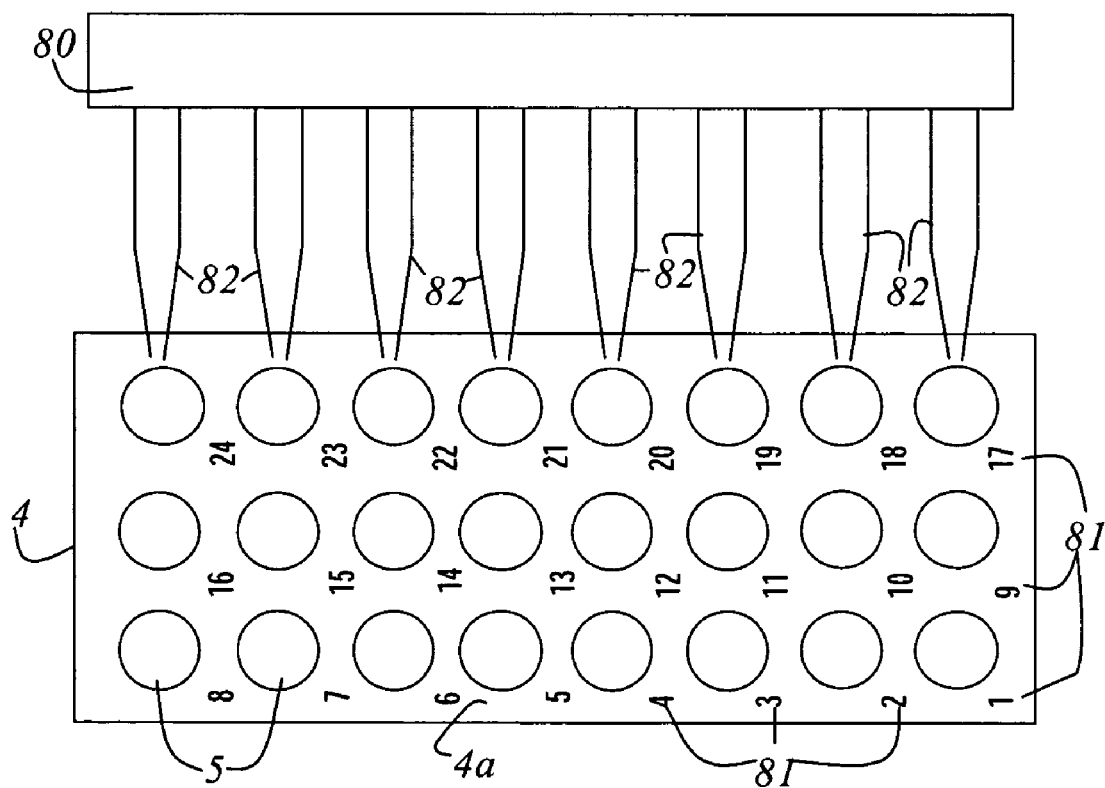
FIG. 4b is a plan view of a further embodiment of a slide, a pipette for the application of liquid droplets likewise being depicted.

FIG. 4a shows an embodiment of a slide that is used in the context of the invention. For identification, slide 4 advantageously possesses an identifier such as the one depicted, for example, in German Utility Model DE 299 06 382 U1. Identifier 4c is mounted on surface 4a of slide 4 and can be embodied in the form of a barcode, transponder, or chip. It is evident to one skilled in the art that numerous possible embodiments exist in terms of the size and shape of slide 4 and the arrangement of depressions 5 on upper side 4a of slide 4. A further embodiment of slide 4 is depicted in FIG. 4b. A rectangular surface of slide 4 having the dimensions 76 mm×26 mm contains, in the Teflon coating of the slide, 8×3 depressions 5 having a diameter of 2 to 3 mm. For recording purposes, a number 81 is associated with each depression 5. Also depicted in FIG. 4b is a multi-channel pipette 80 which allows a defined application of liquid droplets 6 onto slide 4. In addition, the requisite liquid volume can be set very precisely with multi-channel pipette 80, and the application of liquid droplets 6 onto the slide is particularly effective. Since slide 4 possesses three rows each having eight depressions 5, multi-channel pipette 80 likewise has eight individual channels 82, spaced in accordance with depressions 5 on slide 4.

Figure 5:
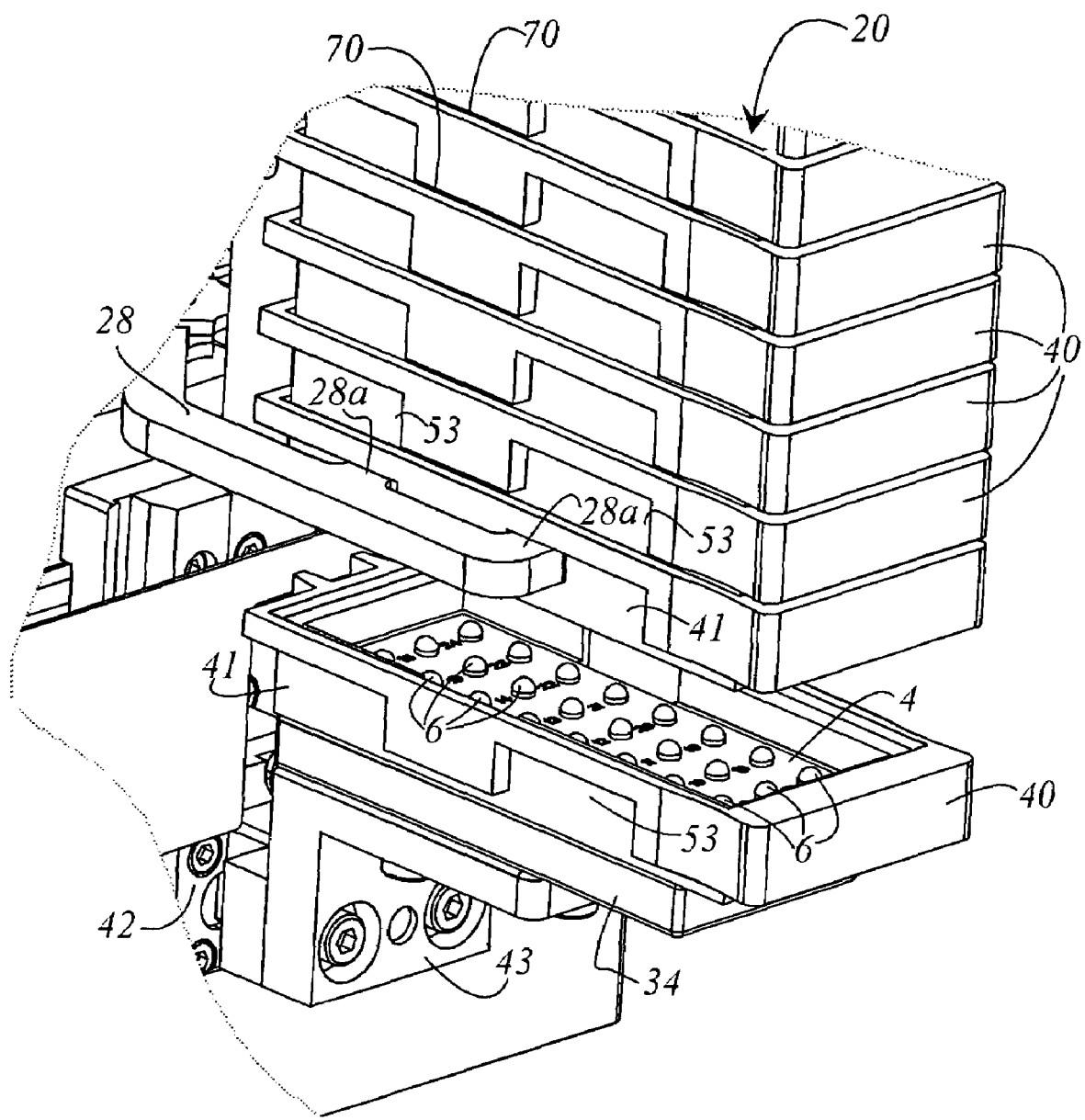
FIG. 5 is a perspective detail view of the coaction of the transport holder with the stack of transport containers in the first or second station.
Figure 6:
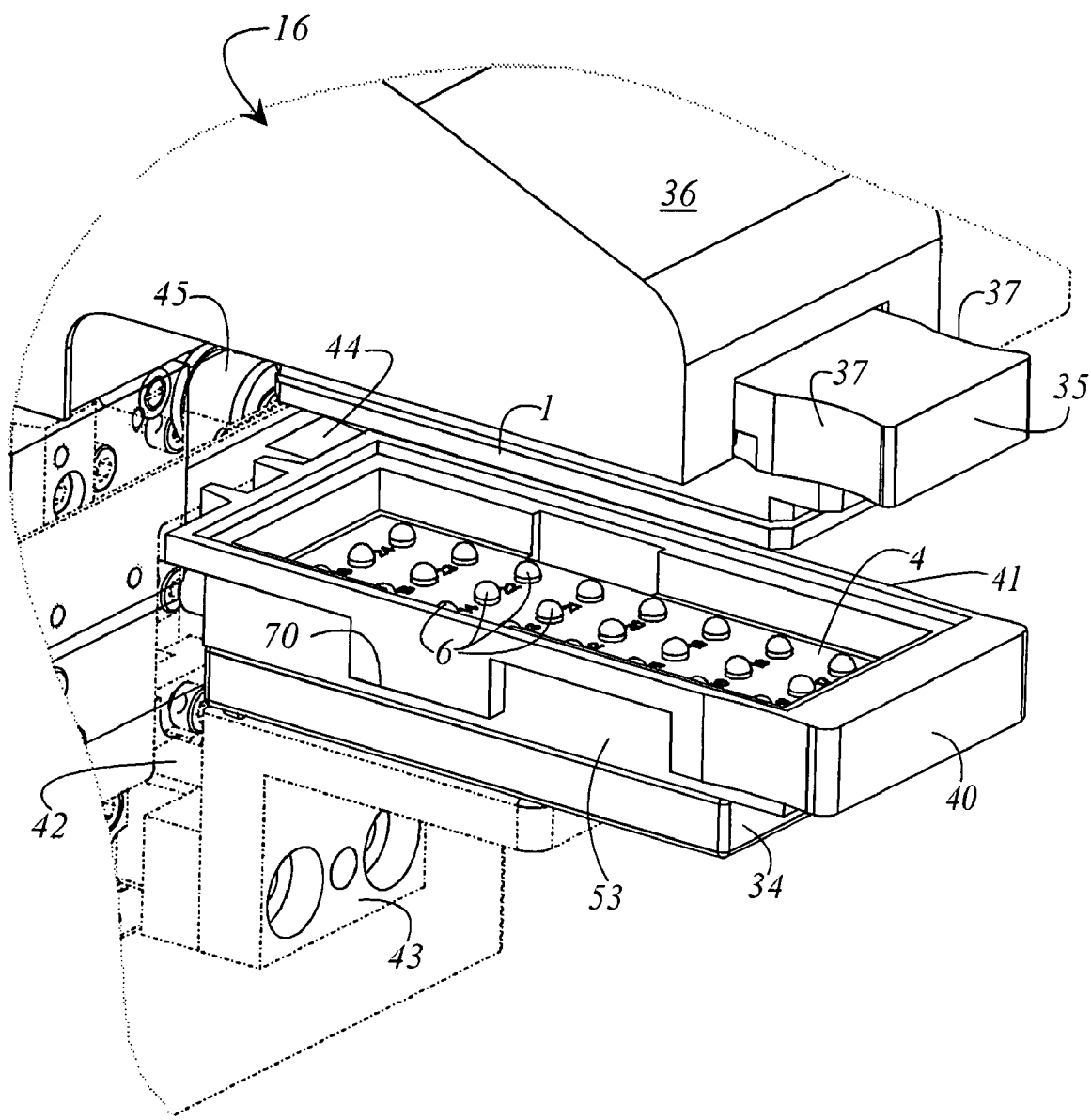
FIG. 6 is a perspective detail view of the coaction of the transport holder with a carrier plate located in the treatment section.
Figure 8:
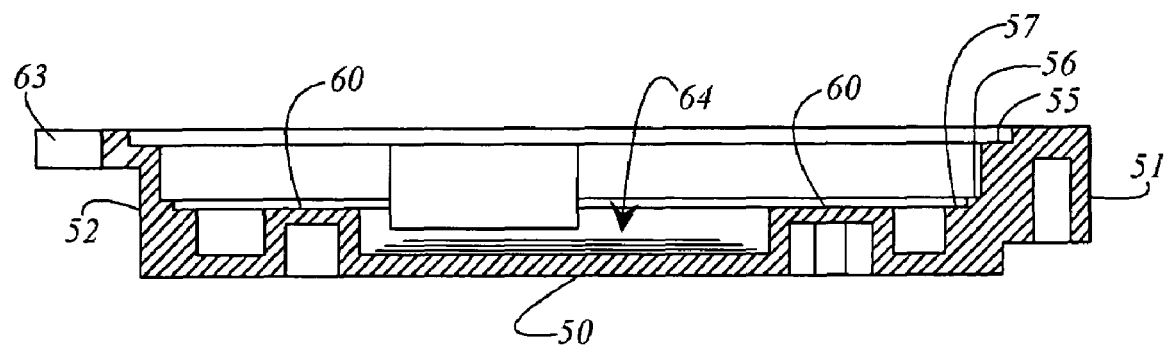

FIG. 8 is a perspective detail view of the coaction of transport holder 34 with a stack 20 of transport containers 40. Stack 20 of transport containers 40 is held by means of a clamp 28. Clamp 28 prevents stack 20 from falling downward. As depicted in FIG. 5, transport holder 34 is located directly beneath stack 20. Transport holder 34 is attached to transport mechanism 42 (not shown here in detail) with a bracket 43. A slide 4 is located in transport container 40 that rests on transport holder 34. Multiple liquid droplets 6 are located on slide 4. In the preferred exemplary embodiment shown here, 3×8 liquid droplets 6 are arranged on slide 4. The bottom most transport container 40 of stack 20 is held by clamp 28 in such a way that clamp 28 coacts with a left and right sidewall 53 and 54 of a peripheral delimiting wall 49 of transport container 40. Clamp 28 has shaped onto it at least one lug 28a that comes into contact with a left and right sidewall 53 and 54 of transport container 40.

Figure 9:
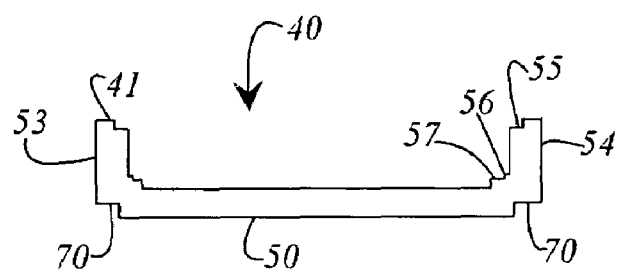
FIG. 9 is a sectioned view of the transport container taken along dashed line 9-9 in FIG. 7b.

FIG. 9 is a perspective detail view of the coaction of transport holder 34 with a carrier plate 1 located in treatment section 16. Transport mechanism 42 and bracket 43 for retaining transport holder 34 for transport containers 40 are depicted with dashed lines. A transport container 40, in which a slide is located, rests on transport holder 34. The positions of liquid droplets 6 on slide 4 located in transport container 40 correspond to the positions of metal grids 2 on carrier plate 1 (see FIG. 1). Carrier plate 1 is retained in treatment section 16 by holder 35, which is attached to arm 36 of treatment section 16. Holder 35 possesses two grip recesses 37 that are used to introduce the holder into arm 36 of treatment section 16 and/or remove it therefrom. The treatment section encompasses means (not depicted) that center the carrier plate from above laterally and in parallel fashion, so that the positions of metal grids 2 and of liquid droplets 6 coincide. Slide 4 is brought closer to carrier plate 1 by transport mechanism 42. At a specific short distance between slide 4 and carrier plate 1, liquid droplets 6 wet metal grids 6 on carrier plate 1, together with tissue sections 2a. The distance between carrier plate 1 and slide 4 depends on the volume of liquid droplets 6. Different volumes for the liquid droplets are advisable because on the one hand washing droplets should be as large as possible in order to achieve a good cleaning effect, while on the other hand labeling solutions with antibodies are very expensive and the volume should thus be kept as small as possible. Transport mechanism 42 can encompass a linear guidance system having a drive system using a stepping motor 45 and position sensors. In order to ensure an accurate distance between carrier plate 1 and slide 6, a sensor 44 is provided that measures the distance from carrier plate 1 to slide 4. Liquid droplets 6 are metered with a pipette so that their volume is accurately determined.

Figure 7A:
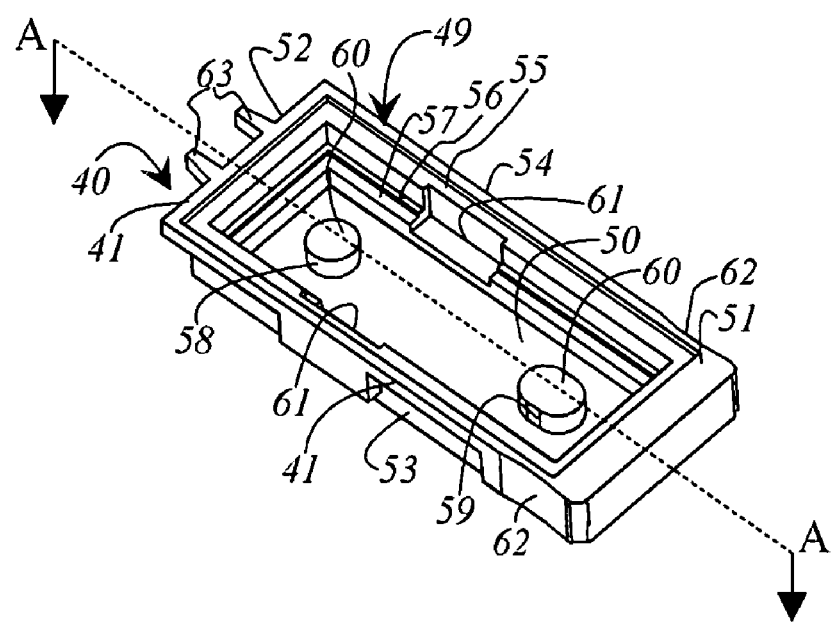
FIG. 7a is a perspective top view of an embodiment of the transport container.

A perspective top view of an embodiment of transport container 40 is depicted in FIG. 7a. Transport container 40 is embodied in the form of a trough that comprises a peripheral delimiting wall 49 which is closed off by a base 50. Transport container 40 is produced from a dimensionally stable material such as, for example, aluminum, composite material, filled polymer material, or unfilled polymer material. As a rule, transport container 40 is produced using an injection-molding method. Other production methods, for example milling, are also conceivable, injection molding being the most cost-effective. The material of which transport container 40 is manufactured is a suitable polymer material (e.g. RYTON BR 111 BL of the Chevron Phillips Chemical Company). Delimiting wall 49 possesses a front wall 51 and a back wall 52, both joined to one another via a left and a right sidewall 53 and 54. Front wall 51 and back wall 52 each form a right angle with left and with right sidewall 53 and 54. Delimiting wall 49 has toward the inside a peripheral first step 55, a peripheral second step 56, and a peripheral third step 57. The next transport container 40 (see FIG. 5) rests with its base 50 on first step 55. Base 50 of the one transport container 40 thus simultaneously constitutes a cover for the next transport container 40 located below it. Slide 4 rests on third step 57 and is simultaneously fixed in position by the edge of second step 56. Base 50 of transport container 40 has a first and a second elevation 58 and 59, each of which possesses a planar flattened area 60. Flattened area 60 is located at the height of third step 57, so that the elevations serve as supports for slide 4. First elevation 58 is round. Second elevation 59 is oval in shape. In addition, a moisture-emitting medium (not depicted in FIG. 7a) can be placed onto base 50 of transport container 40. Left and right sidewalls 53 and 54 each have a protrusion 61. In the region of protrusion 61, slide 4 is not completely in contact against left and right sidewalls 53 and 54 so that, for example, moisture from the moisture-emitting medium on base 50 of transport container 40 can reach the surface of slide 4 that carries liquid droplets 6. Protrusions 61 likewise facilitate the removal of slide 4 from transport containers 40. Left and right sidewalls 53 and 54 of transport container 40 possess, in the region of its front wall 51, two grip recesses 62 that ensure reliable handling of transport container 40 for the user. Back wall 52 of transport container 40 has two parallel lugs 63 shaped onto it. Lugs 63 serve as a guide in an apparatus that can automatically process the transport containers.

Figure 7B:
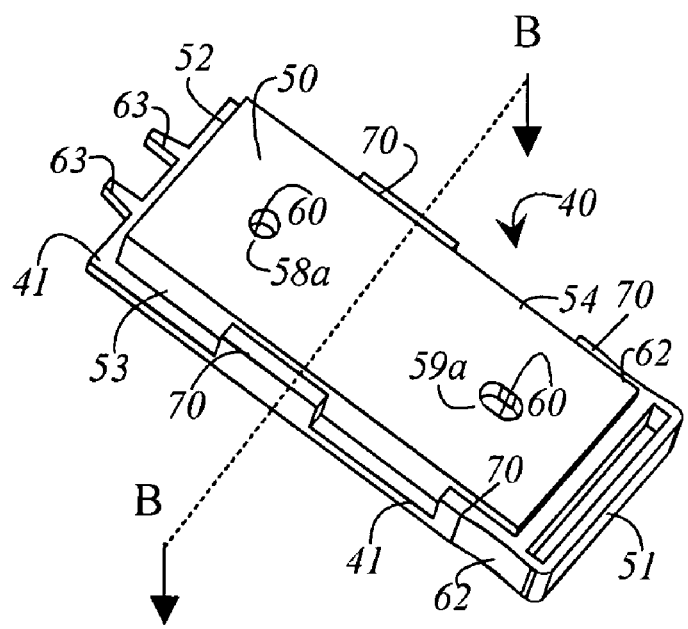
FIG. 7b is a perspective bottom view of an embodiment of the transport container.

FIG. 7b is a perspective bottom view of the embodiment of transport container 40 depicted in FIG. 7a. First elevation 58 and a second elevation 59 are not configured in solid fashion. First elevation 58 possesses a depression having a cross section in the shape of a circle 58a. Second elevation 59 possesses a depression having a cross section in the shape of an elongated hole 59a. Both depressions end in the region of planar flattened area 60. The depressions serve to position transport container 40 on transport holder 34. Two pins (not depicted) that position transport container 40 on transport holder 34 by engagement of the pins into the depressions are shaped onto transport holder 34 for that purpose. Left sidewall 53, back wall 52, and right sidewall 54 are equipped with a rim 41. At least one stop 70 is embodied respectively on left sidewall 52 and on right sidewall 54. Stop 70 can serve, for example in stack 20 of transport containers 40, to ensure reliable placement on transport container 40 located therebeneath.

FIG. 8 is a further sectional view of transport container 40 taken along line 8-8 of FIG. 7a. It is clearly evident that third step 57 lies at the same level as flattened area 60 of first and second elevations 58 and 59. As already mentioned in the description of FIG. 7a, a moisture-emitting medium 64 is provided on base 50 of transport container 40 so that the moisture prevents liquid droplets (see FIG. 5) from drying out.

FIG. 9 is a further sectional view of transport container 40 taken along line 9-9 of FIG. 7b. Transport container 40 possesses a substantially U-shaped profile along section line 9-9 left sidewall 53 and right sidewall 54 constituting the limbs of the U-shaped profile. Stops 70 are spaced away from base 50 of the transport container. Delimiting wall 49 of left and of right sidewall 53 and 54 has, toward the inside, a peripheral first step 55, a peripheral second step 56, and a peripheral third step 57. The next transport container 40 (see FIG. 5) rests with its base 50 on first step 55. Base 50 of the one transport container 40 thus simultaneously constitutes a cover for the next transport container 40 located below it. Slide 4 rests on third step 57 and is simultaneously fixed in position by the edge of second step 56.

What is claimed is:

1. A transport container for slides for immunological labeling of thin tissue sections comprising: a left and a right sidewall, a backwall and a frontwall joined together to form a peripheral delimiting wall having interior and exterior sides, a base attached to the peripheral delimiting wall closing off the transport container, at least one peripheral step formed in the interior side of the peripheral delimiting wall, and wherein said base comprises first and second elevations and a planar flattened area located at the same level as the slide for providing additional support to said slide, said first and second elevations being cup-shaped with a depression closed off by said planar flattened area, said depression of said first elevation having a cross-section in the form of a circle, and the depression of the second elevation having a cross-section in the form of a rectangle with rounded edges.

2. The transport container as defined in claim 1, wherein said at least one peripheral step in said interior side of said peripheral delimiting wall is continuous.

3. The transport container as defined in claim 2, wherein at least one stop is embodied respectively on the left sidewall and on the right sidewall.

4. The transport container as defined in claim 1, wherein the transport container is stackable in a stack, such that the base of one transport container constituting in each case the cover for a transport container located beneath it.

5. The transport container as defined in claim 1, wherein the delimiting wall of the transport container has embodied on it in the region of the front wall two grip recesses that are arranged opposite one another.

6. The transport container as defined in claim 1, wherein the delimiting wall of the transport container has shaped on it in the region of the back wall two parallel lugs that serve partially as guides for arranging the transport container in the stack.

7. The transport container as defined in any of claim 1, wherein the delimiting wall has embodied in the left and the right sidewall at least one protrusion in each case, operatively arranged so the slide does not contact the left or right sidewall in the region of the protrusion.

8. The transport container as defined in claim 1, wherein the transport container is fabricated from a dimensionally stable material.

9. The transport container as defined in claim 8, wherein the transport container is injection molded.

* * * * *